(12) United States Patent
Schubert et al.

(10) Patent No.: US 10,048,059 B1
(45) Date of Patent: Aug. 14, 2018

(54) COMBINED USE OF OSCILLATING MEANS AND ELLIPSOMETRY TO DETERMINE UNCORRELATED EFFECTIVE THICKNESS AND OPTICAL CONSTANTS OF MATERIAL DEPOSITED AT OR ETCHED FROM A WORKING ELECTRODE THAT PREFERRABLY COMPRISES NON-NORMAL ORIENTED NANOFIBERS

(71) Applicants: Mathias M. Schubert, Lincoln, NE (US); Tino Hofmann, Harrisburg, NC (US); John A. Woollam, Lincoln, NE (US); Rebecca Y. Lai, Lincoln, NE (US)

(72) Inventors: Mathias M. Schubert, Lincoln, NE (US); Tino Hofmann, Harrisburg, NC (US); John A. Woollam, Lincoln, NE (US); Rebecca Y. Lai, Lincoln, NE (US)

(73) Assignees: J. A. WOOLLAM CO., INC, Lincoln, NE (US), part interest; THE BOARD OF REGENTS OF THE UNIVERSITY OF NEBRASKA, Lincoln, NE (US), part interest ( * ) Notice: Subject to any disclaimer, the term of this patent is extended or adjusted under 35 U.S.C. 154(b) by 258 days.

(21) Appl. No.: 15/330,127

(22) Filed: Aug. 11, 2016

Related U.S. Application Data

(60) Provisional application No. 62/283,115, filed on Aug. 21, 2015.

(51) Int. Cl.
  *G01B 11/06* (2006.01)
  *G01N 27/42* (2006.01)
  (Continued)

(52) U.S. Cl.
  CPC ............. *G01B 11/06* (2013.01); *C25B 3/04* (2013.01); *C25B 11/0405* (2013.01);
  (Continued)

(58) Field of Classification Search
  CPC ...... G01N 21/21; G01N 21/211; G01N 21/23; G01N 21/25; G01N 21/272; G01N 21/29;
  (Continued)

(56) References Cited

U.S. PATENT DOCUMENTS 3,975,238 A * 8/1976 Bean ................... G01N 21/211
                                                  204/403.14
4,561,286 A    12/1985 Sekler et al.
(Continued)

OTHER PUBLICATIONS

Svoboda, Vojtech et al., "In situ transient study of polymer film growth via simultaneous correlation of charge, mass, and ellipsometric measurements," 2008, Pure Appl. Chem., vol. 80, No. 11, pp. 2439-2449.*
(Continued)

*Primary Examiner* — Gordon J Stock, Jr.
(74) *Attorney, Agent, or Firm* — James D. Welch

(57) ABSTRACT

Disclosed are systems and methods that enable determination of uncorrelated thickness of a working electrode and surface region optical constants in settings involving electrochemical processing at a working electrodes in a Piezoelectric Balance system, by simultaneous application of an Ellipsometer system, the working electrode optionally having a multiplicity of nanofibers that are oriented non-normally to a surface of said working electrode. Further disclosed is, simultaneous with said determinations, the monitoring of electrochemical processes at a piezoelectric balance working electrode driven by electrical energy applied between said working electrode and counter electrode.

24 Claims, 11 Drawing Sheets

(51) Int. Cl.
*G01N 27/27* (2006.01)
*G01N 21/21* (2006.01)
*C25B 11/04* (2006.01)
*C25B 3/04* (2006.01)
*G01J 4/00* (2006.01)

(52) U.S. Cl.
CPC ........ *C25B 11/0415* (2013.01); *G01N 21/211* (2013.01); *G01N 27/27* (2013.01); *G01N 27/42* (2013.01); *G01J 2004/001* (2013.01)

(58) Field of Classification Search
CPC .. G01N 21/31; G01N 21/41; G01N 2021/212; G01N 2021/213; G01N 2021/214; G01N 2021/217; G01N 2021/218; G01N 2021/4126; G01N 27/26; G01N 27/27; G01N 27/28; G01N 27/416; G01N 27/4116; G01N 27/42; G01N 27/426; G01B 11/06; G01B 11/0616; G01B 11/0625; G01B 11/0633; G01B 11/0641; G01B 11/065; G01B 11/0683; G01J 3/0224; G01J 3/28; G01J 3/2803; G01J 3/2823; G01J 3/42; G01J 3/447; G01J 3/46; G01J 4/00; G01J 4/02; G01J 4/04; G01J 2004/001; G01J 2004/002; G01J 2004/004; G01J 2004/005; G01J 2004/007; G01J 2004/008; C25B 3/02; C25B 3/04; C25B 9/16; C25B 11/0405; C25B 11/041; C25B 11/0415; C25B 11/0442; C25B 11/0447; C25B 11/0478; C25B 11/0489; C25B 11/12
USPC ................................ 356/364–370, 630–632
See application file for complete search history.

(56) References Cited

U.S. PATENT DOCUMENTS

| | | | |
|---|---|---|---|
| 4,735,081 A | 4/1988 | Luoma et al. | |
| 4,807,994 A | 2/1989 | Felch et al. | |
| 5,373,359 A | 12/1994 | Woollam et al. | |
| 5,666,201 A | 9/1997 | Johs et al. | |
| 5,706,212 A | 1/1998 | Thompson et al. | |
| 5,872,632 A | 2/1999 | Moore | |
| 5,963,327 A | 10/1999 | He et al. | |
| 6,034,777 A | 3/2000 | Johs et al. | |
| 6,125,687 A | 10/2000 | McClelland et al. | |
| 6,353,477 B1 | 3/2002 | Johs et al. | |
| 6,456,376 B1 | 9/2002 | Liphardt et al. | |
| 7,030,982 B1* | 4/2006 | Woollam ............ | G01B 11/0641 356/369 |
| 2004/0256961 A1 | 12/2004 | Namba et al. | |
| 2004/0257567 A1 | 12/2004 | Woollam et al. | |
| 2008/0163688 A1* | 7/2008 | Wang .................. | G01N 21/553 73/580 |

OTHER PUBLICATIONS

Broch, Laurent et al., "Real time in situ ellipsometric and gravimetric monitoring for electrochemistry experiments," 2007, Review of Scientific Instruments, 78, pp. 064101-1 to 064101-6.*
Rodenhausen, K.B. et al., "Combined optical and acoustical method for determination of thickness and porosity of transparent organic layers below the ultra-thin film limit," 2011, Review of Scientific Instruments, 82, pp. 103111-1 to 103111-10.*
Xu, Yuanjin et al., "Simultaneous UV-visible spectroelectrochemical and quartz crystal microgravimetric measurements during the growth of poly(1-naphthylamine) film," 1995, Journal of Electroanalytical Chemistry, 389, pp. 85-90.*
Tjarnhage, Torbjorn et al., "Liposome and phospholipid adsorption on a platinum surface studies in a flow cell designed for simultaneous quartz crystal microbalance and ellipsometry measurements," 1996, Colloids and Surfaces B: Biointerfaces, 8, pp. 39-50.*
Buron, C.C. et al., "Mass and charge balance in self-assembled multilayer films on gold. Measurements with optical reflectometry and quartz crystal microbalance," 2006, Journal of Colloid and Interface Science, 296, pp. 409-418.*
Berkes, Balazs B. et al., "Combination of nanogravimetry and visible spectroscopy: A tool for the better understanding of electrochemical processes," 2014, Journal of Electroanalytical Chemistry, 719, pp. 41-46.*
Zimmer, Alexandre et al., "In situ analysis of bismuth telluride electrodeposition using combined spectroscopic ellipsometry and electrochemical quartz crystal microbalance," 2007, Electrochimica Acta, 52, pp. 4760-4766.*
"Surace Specific Kinetics of Lipid Vesicle Adsorbtion Measured With a Quartz Microbalance", Keller et al., Biophysical Journal, vol. 75, (1998), pp. 1397-1402.
"Characterization of PNA and DNA Immobilization and Subsequent Hybridization with DNA Using Acoustic Shear-Wave Attenuation Measurements", Hook et al., Langmuir 17, (2001), pp. 8305-8312.
"Simultaneous Monitoring of Protein Adsorbtion at the Solid-Liquid Interface From Sessile Solution Droplets by Ellipsometry and Axisymmetric Drop Shape Analysis by Profile", Noordmans et al., Colloids and Surfaces B: Biointerfaces 15, (1999), pp. 227-233.

* cited by examiner

COMBINED USE OF OSCILLATING MEANS AND ELLIPSOMETRY TO DETERMINE UNCORRELATED EFFECTIVE THICKNESS AND OPTICAL CONSTANTS OF MATERIAL DEPOSITED AT OR ETCHED FROM A WORKING ELECTRODE THAT PREFERRABLY COMPRISES NON-NORMAL ORIENTED NANOFIBERS

This Application Claims Benefit of Provisional 62/283,115 Filed Aug. 21, 2015.

TECHNICAL FIELD

The present invention relates to systems and methods for determining uncorrelated thickness and optical constants of samples, as well as investigate cyclical applied voltage effects; and more particularly to systems and methods that involve electrochemical processing at a working electrode in a Piezoelectric Balance system with simultaneous application of an Ellipsometer system, said working electrode optionally comprising a multiplicity of nanofibers that are oriented normal or non-normal to a surface thereof. The present invention also includes non-electrochemical processing of a Piezoelectric Balance working electrode which includes a multiplicity of nanofibers at a surface of a working electrode, simultaneous with application of an Ellipsometer system.

BACKGROUND

It is known to apply Piezoelectric Balances as a means to monitoring change of mass of an electrode thereof, and thereby allow determination of an effective thickness of said electrode during processing that changes said electrode mass. Known relevant references are EP 0676637 and EP 2008067.

The 637 reference describes application of a Piezoelectric Balance Working Electrode in the context of an Electrochemical Cell. Changes in working electrode mass resulting from electrochemical processes in said Electrochemical Cell cause change in the vibrational frequence of the Piezoelectric Balance system, and said frequency changes can be interpreted to describe said working electrode mass change, and that allows determining electrode effective thickness. Said 637 reference, however, makes no mention of simultaneous use of an Ellipsometer system to then, knowing the effective thickness, arrive at uncorrelated optical constants. Additional known Patents and Published Applications are: U.S. Pat. Nos. 4,561,286; 4,735,081; 4,807,994; 5,373,359; 5,666,201; 5,706,212; 5,872,632; 5,963,327; 6,034,777; 6,125,687; 6,353,477; 6,456,376; 2004/0256961 and 2004/0257567. Known Articles are "Surface Specific Kinetics of Lipid Vesicle Adsorbtion Measured with a Quartz Balance", Keller et al., Biophysical Journal, Vol. 75 (1998); "Simultaneous Monitoring of Protein Adsorbtion at Solid-Liquid Interface from Sessile Solution Droplets by Ellipsometry and Axisymetric Drop Shape Analysis by Profile", Noordmans et al., Colloids and Surfaces B: Biointerfaces 15, (1999); and "Characterization of PNA and DNA Immobilization and SUubsequent Hybridization with DNA Using Acoustic Shear wave Attenuation Measurements", Hook et al., Langmuir 17, (2001).

The 067 reference does describe simultaneous use of a Piezoelectric Balance comprising a working electrode, and Ellipsometer system, to arrive at uncorrelated effective thickness and optical constants of a mass on said working electrode which is disposed in a system cell that allows a fluid, (eg. analyte containing liquid), to access said electrode and, for instance, to enter thereinto and deposit analyte onto said working electrode.

Importantly, neither identified relevant reference suggests use of a working electrode that has a multiplicity of nanofibers projecting therefrom, at a normal or non-normal orientation to said working electrode. The presence of such normal or non-normal oriented nanofibers enables determining anisotropic properties, as indicated by the presence of Off-axis Elements in Jones or Mueller Matricies determined from data provided by a present Ellipsometer.

It is also noted that when working with biological samples repeatability can be a problem. That is, while two essentially identical samples can be prepared and subjected to what are identical processes, results often do not match one experiment to the next. A system and method or it's use that enables taking data that decouples optical constants and sample thickness, simultaneous with taking data that relates to sample changes to application of an electrochemical reaction driven voltage pattern, (eg. cycles to induce hysteresis loops), would therefore provide great utility.

DISCLOSURE OF THE INVENTION

The present invention is a system for dynamically determining uncorrelated effective thickness and optical constants for a mass on a surface of a working electrode in a piezoelectric balance, and which enables simultaneous investigation of electrochemical driven reactions as a function of applied electrical energy. Said piezoelectric balance comprises said working electrode that responds by vibrating when a potential is applied thereto, the frequency of vibration of the piezoelectric balance working electrode being dependent on the mass thereof. Said working electrode is a component of an electrochemical cell, said electrochemical cell comprising an entry port for entering an electrolyte thereinto and a counter electrode. In use an electrolyte is entered into said entry port and contacts said working electrode, such that when electrical energy is applied between said working electrode and said counter electrode an electrochemical reaction occurs at the working electrode, thereby causing a change in the vibrational frequency of said piezoelectric balance which is representative of a change in mass of, and thereby the effective thickness thereof, as a result of electrochemical reaction. Said system further comprises a source of electromagnetic radiation which is oriented to simultaneously direct a beam of electromagnetic radiation therefrom at the surface of said working electrode, interact therewith and enter a detector of electromagnetic radiation that produces data which, knowing the effective thickness of the mass at said working electrode, enables determining associated, uncorrelated optical constants for the effective thickness of the mass of the working electrode.

Said further comprises an exit port for flowing electrolyte out of said electrochemical cell to expel excess volume of electrolyte entered thereto.

The working electrode can comprise a multiplicity of nanostructures projecting from said working electrode surface normal, or non-normal thereto.

The source of electromagnetic radiation and detector thereof are typically elements of an ellipsometer system that comprise polarization state generating and polarization state analyzing elements ahead of and after said working electrode, respectively.

The multiplicity of nanostructures at the surface of the working electrode preferably project non-normal therefrom.

The piezoelectric material comprising the working electrode is preferably quartz.

The effective thickness of said mass of said working electrode can be changed as a result of deposition of an analyte from said fluid thereonto from said fluid, or by etching material therefrom as a result of interaction with said fluid.

The system can further comprise a reference electrode which is applied to establish a reference potential from which the potential applied between the working and counter electrodes can be calibrated.

A method of dynamically determining uncorrelated effective thickness and optical constants for a mass on a surface of a working electrode in a piezoelectric balance, and enables simultaneous investigation of electrochemical driven reactions as a function of applied electrical energy, comprising:

a) providing a system as just described;

b) causing electrolyte to flow into said entry port of said electrochemical cell and interact with said surface of said working electrode, while applying electrical energy between said counter and working electrodes; and applying vibration effecting potential to the working of said piezoelectric balance;

c) simultaneously with step a) causing said source of electromagnetic radiation to direct a beam of electromagnetic radiation so that it interacts with said surface of said working electrode and enter said detector of electromagnetic radiation;

d) gleaning effective thickness of said mass of said working electrode and with that known, determining optical constants of said mass of said surface of working electrode.

Said method can provide that the step of providing a system further involves providing a working electrode that comprises a multiplicity of nanostructures projecting normally or non-normally from said surface of said working electrode.

Said method can provide that the step of providing a system further involves providing an exit port for flowing electrolyte out of said electrochemical cell.

Said method can involve the effective thickness of said mass of said working electrode is changed as a result of deposition of an analyte from said electrolyte thereonto, or as the result of etching material therefrom as a result of interaction with said electrolyte.

Said method can involve that the step of providing a system further involves providing a reference electrode which is applied to establish a reference potential from which the potential applied between the working and counter electrodes can be calibrated.

Another recitation of a present invention method of dynamically determining uncorrelated effective thickness and optical constants for a mass on a surface of a working electrode in a piezoelectric balance, and enables simultaneous investigation of electrochemical driven reactions as a function of applied electrical energy, comprises:

a) providing a system as described above but is further distinguished in that the surface of said working electrode comprises a multiplicity of nanostructures projecting non-normally therefrom;

b) entering a fluid into said entry port of said cell and interact with said surface of said working electrode while applying vibration effecting potential to said working electrode of said piezoelectric balance;

c) simultaneously with step a) causing said source of electromagnetic radiation to direct a beam of electromagnetic radiation so that it interacts with said surface of said working electrode and enter said detector of electromagnetic radiation;

d) gleaning effective thickness of said mass of said working electrode and with that known, determining optical constants of said mass of said surface of working electrode.

Said method can involve the step of providing a system further involves providing an exit port for flowing electrolyte out of said electrochemical cell.

Said method can involve the effective thickness of said mass of said working electrode is changed as a result of deposition of an analyte from said electrolyte thereonto from said fluid, or by etching material therefrom as a result of interaction with said electrolyte.

Said method can involve the step of providing a system further involves providing a reference electrode which is applied to establish a reference potential from which the potential applied between the working and counter electrodes can be calibrated.

Said method can comprise determining at least partial Jones or Mueller Matricies from data provided by the detector of electromagnetic radiation in the process of determining optical constants. Said method can involve that at least one off-diagonal Jones or Mueller matrix element is determined. This is especially relevant when non-normal nanostructures are present on the surface of the working electrode.

A very important point is that any present invention methodology can further comprise varying the voltage applied between the working electrode and counter electrode, while also simultaneously obtaining data regarding the frequency of vibration of said working electrode and ellipsometric data vs. said applied voltage between said working electrode and said counter electrode so that an electrochemical reaction occurs at the working electrode. This enables simultaneous determination of uncorrelated sample optical constants and sample thickness, as well as sample changes as a function of applied voltage between said working electrode and said counter electrode.

The foregoing Methodology can also comprise determining at least partial Jones or Mueller Matricies from data provided by the detector of electromagnetic radiation in the process of determining optical constants an that at least one off-diagonal Jones or Mueller matrix element is determined.

The present invention will be better understood by reference to the Detailed Description of this Specification, in conjunction with the Drawings.

DETAILED DESCRIPTION

Figure 1A:
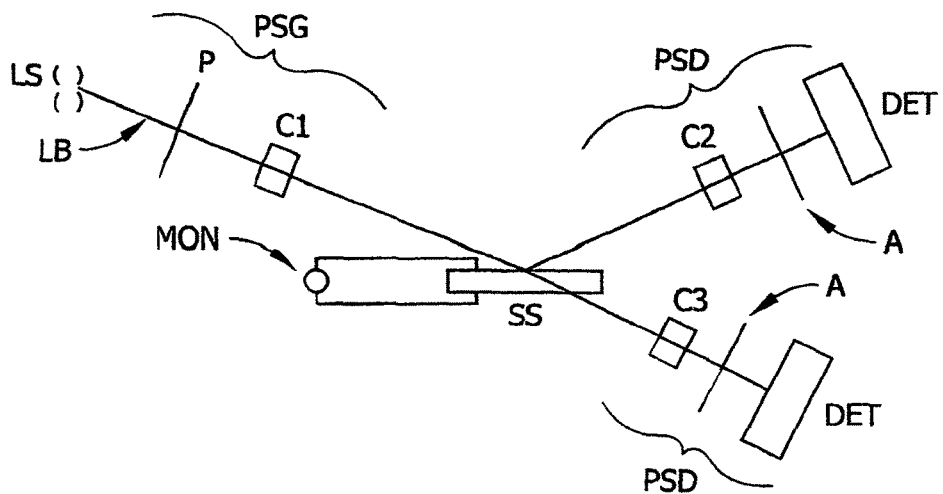
FIG. 1A shows a prior art environmental chamber for investigating a sample therewithin with an ellipsometer system.

FIG. 1A shows generally a prior art Ellipsometer system for investigating a sample. Note that a Source of Electromagnetic Radiation (LS) provides a beam (LB) which has a polarization state set by a Polarizer (P) and optional Compensator (C1) prior to interaction with a Sample (SS). Shown after the Sample (SS) are both reflection and transmission scenarios, each of which comprises an Analyzer (A) and optional Compensator (C2) (C3). Indications of Polarization State Generator (PSG) and Polarization State Detector (PSD) are also shown.

Figure 1B:
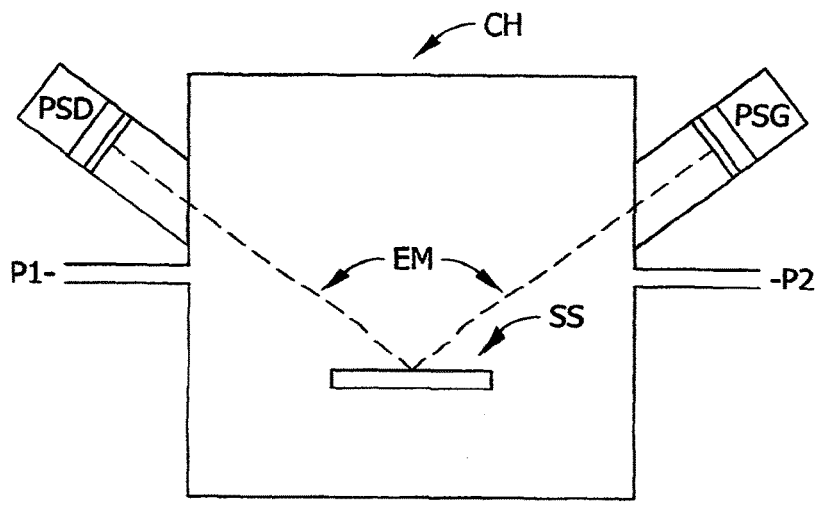
FIG. 1B shows the basic components of a prior art ellipsometer system applied to investigating a sample in reflection or transmission, with indication of a frequency monitoring system.
Figure 1C:
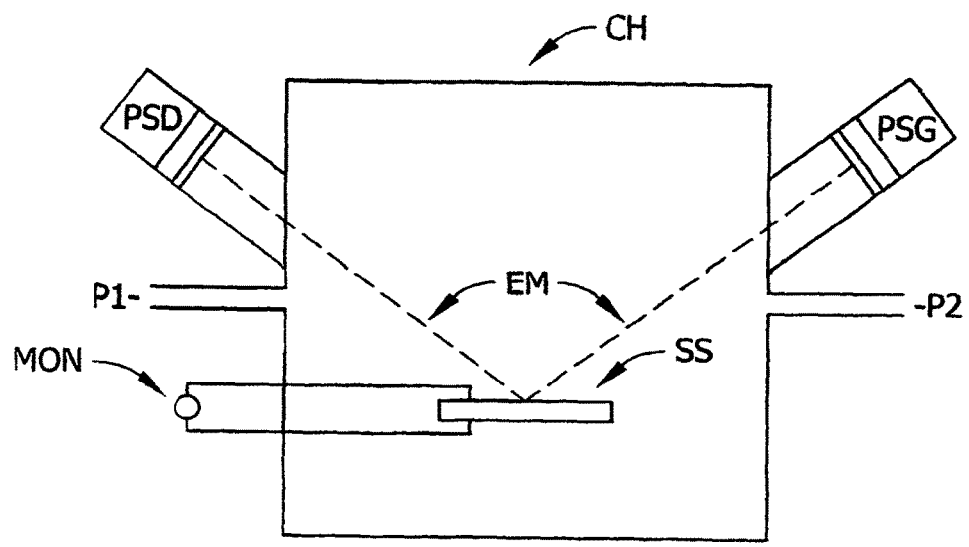
FIG. 1C shows that a FIG. 1A configuration can be fitted with a Monitor (MON) electrically connected to said Sample (SS). Said Monitor (MON) includes excitation and resonant frequency detecting capability.
Figure 1D:
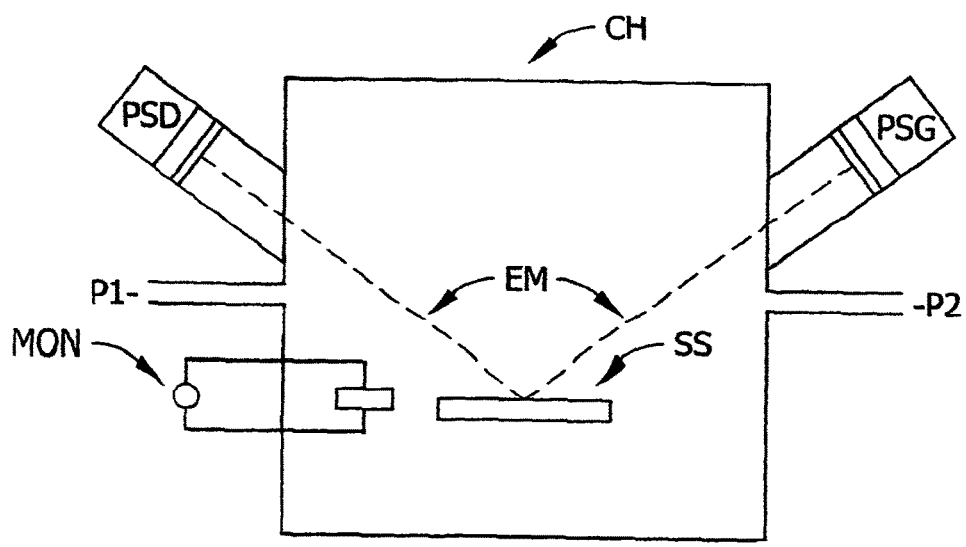
FIG. 1D shows that a FIG. 1A configuration can be fitted with a Monitor (MON) electrically connected to a separate Witness Sample (WS). As in the FIG. 1C configuration said Monitor (MON) includes excitation and resonant frequency detecting capability.

FIG. 1B demonstrates a system for depositing material onto a Sample (SS) from a fluid entered via Port (P1) or (P2). Shown are a Chamber (CH) to which are affixed Polarization State Generator (PSG) and Polarization State Detector (PSD), as well as Ports (P1) and (P2) for entry and exit of material containing fluids for deposition onto Sample (SS), or at least release in the vicinity thereof. It is noted that materials to be deposited can be dielectrics, metals, insulators, etc., or can be organic materials, and the Sample (SS) can have a surface which has affinity for the deposited material entered in a flow of liquid. Typical application of ellipsometry in a FIG. 1A configuration provides data that identifies a product of a thickness and refractive index of, for instance, a thin film deposited on the upper surface of the shown Sample (SS). FIG. 1C shows that a FIG. 1A configuration can be fitted with a Monitor (MON) electrically connected to said Sample (SS). Said Monitor (MON) includes excitation and resonant frequency detecting capability. FIG. 1D shows that a FIG. 1A configuration can be fitted with a Monitor (MON) electrically connected to a separate Witness Sample (WS). As in the FIG. 1C configuration said Monitor (MON) includes excitation and resonant frequency detecting capability. In use, it is know that a. resonant frequency change will occur when material is deposited onto the Sample (SS) or Witness Sample (WS).

As indicated, FIGS. 1A-1D are prior art and, while enabling investigation of a sample while material is deposited thereonto, to the end that uncorrelated refractive index and thickness of a deposited thin film, they do not provide for applying a reaction driving voltage at the sample (SS).

Figure 1E:
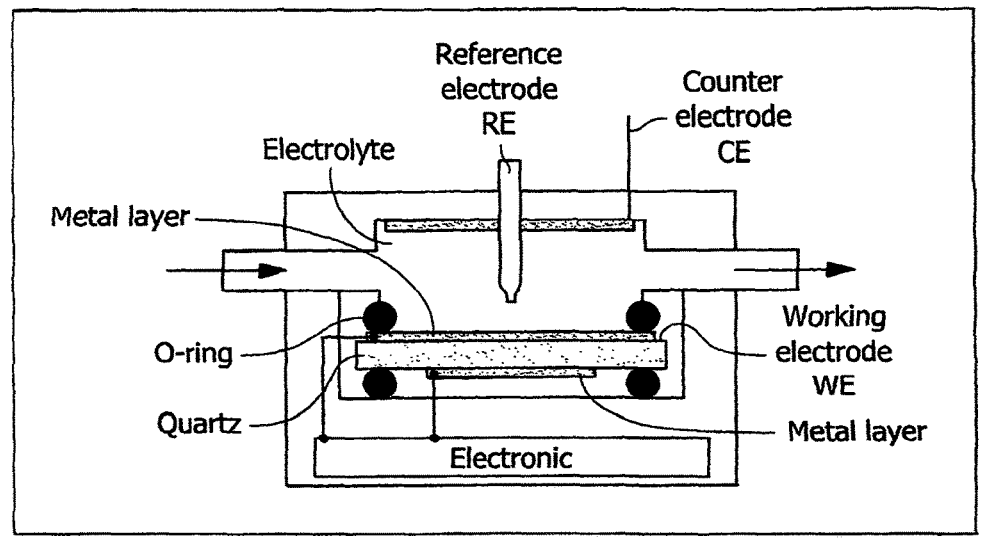
FIG. 1E shows a general view of a prior art piezoelectric balance system useful in monitoring mass accumulation onto a sample via change in vibrational frequency.

FIG. 1E shows a general view of a prior art piezoelectric balance system in a chamber which is useful in monitoring mass accumulation onto a sample via change in vibrational frequency, and which also allows for applying a reaction driving voltage between the Working Electrode (WE) and a Reference Electrode (RE). What is not suggested by the FIG. 1E prior art, however, is that an Ellipsometer system should be incorporated thereinto.

Figure 1F:
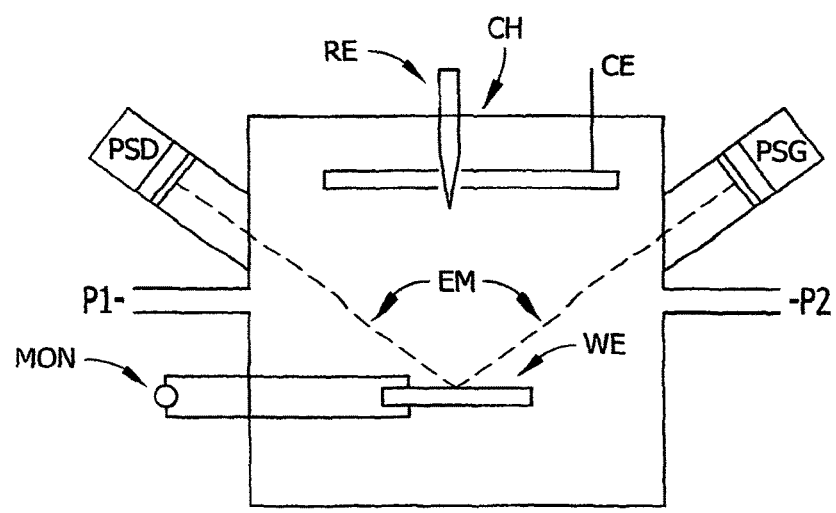
FIG. 1F shows how the prior art system in FIG. 1C is fitted with a Counter Electrode and Reference Electrode to arrive at a system as applied in the present invention.

FIG. 1F shows how the prior art system in FIG. 1C is fitted with a Counter Electrode (CE), and Reference Electrode (RE) to arrive at a present invention system. The FIG. 1G system is distinguished over the prior art in that it combines a FIG. 1B system, including the Ellipsometer (ie. said (PSG and (PSD)), with a FIG. 1E Counter (CE) and Reference Electrodes (RE), and identifies the Sample in FIG. 1B as the Working Electrode (WE). The Inventors know of no prior art that obviates the combination of a Piezoelectric-balance in a Chamber (CH) that allows entry of a sample that interacts with a Working Electrode (WE), while an electric potential is applied between said Working Electrode (WE) and a Counter Electrode (CE), and that further provides for investigation of chemical changes that occur at the Working Electrode (WE) with electromagnetic radiation, such as provided by an Ellipsometer beam of electromagnetic radiation (EM).

Figure 2A:
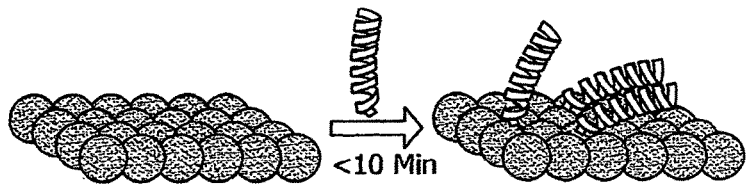
FIGS. 2A and 2B show a sequence of forming an electrochemically active layer of Methyl Blue which can be reduced electrochemically to Leucomethylene.
Figure 2B:
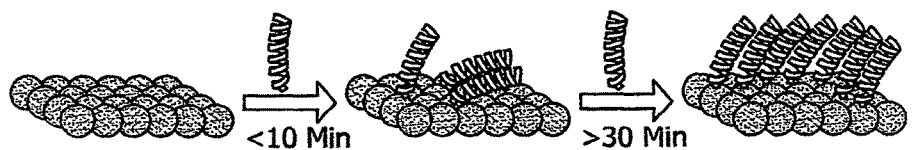

As a very interesting example of applying the present invention system, FIGS. 2A and 2B show a sequence of forming an electrochemically active layer of Leucomethylene Blue (LMB) on such as a Working Electrode (WE) of a Present Invention System as in FIG. 1G. This is particularly relevant to the present invention as a layer of Leucomethylene Blue (LMB) on such as a Working Electrode (WE) provides projections therefrom that are non-normal to the surface of the Working Electrode (WE). Such non-normal projections are useful in the present invention as material deposited thereonto can be investigated as regards anisotropicity as seen in changes in off-axis Jones or Mueller Matrix elements. The present invention is not limited to this approach to providing such non-normal projections from the surface of a Working Electrode (WE). Other techniques can be applied to produce such a result, such as deposition of nanofibers at an oblique angle to the surface of a Working Electrode (WE).

Continuing, FIGS. 2A-2B show that beginning with Methylene Blue (MB) on a sample surface in FIG. 2A, electrochemical reduction to Leucomethylene Blue (LMB) can be accomplished by application of a voltage between a FIG. 1G Working Electrode (WE) and Counter Electrode (CE). In the present example FIG. 2A indicates that the Methylene Blue (MB) is incorporated onto a such as a working Electrode (WE), (as shown in FIGS. 1E and 1G), which Working Electrode (WE) can consist of gold), by attachment to a self-assembled monolayer of hydroxyl terminated $(CH2)6$ chains as well as $(CH2)6$, (see FIG. 2B). It is noted in FIG. 2B that the Leucomethylene Blue (LMB) molecules project at an angle to the plane of the original flat Methylene Blue (MB) molecules. The presence of such fibers at an oblique angle to a sample surface enables acquisition of data as shown in, for instance, FIGS. 7B and 8B, (corresponding to the scenarios in FIG. 2B, which differ from that in FIGS. 7A and 8B, (corresponding to the scenario at the outset in FIG. 2A), as a result of the effect of said nanofibers shifting energy into off-axis elements of a Mueller Matrix. Once nanofibers as in FIG. 2B are present on a sample surface, interactions taking place on the sample can be investigated by reference to changes in said off-diagonal elements.

Figure 3A:
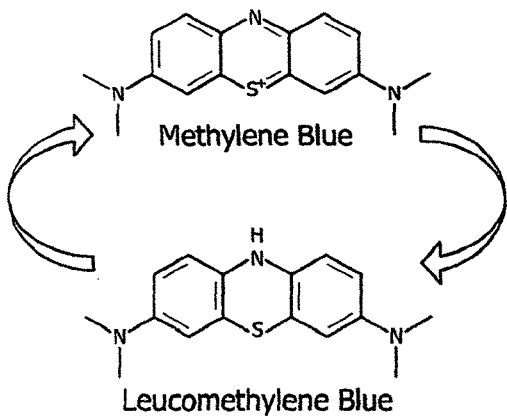
FIGS. 3A and 3A show electrochemical reduction of Methylene Blue to Leucomethylene Blue.
Figure 3B:
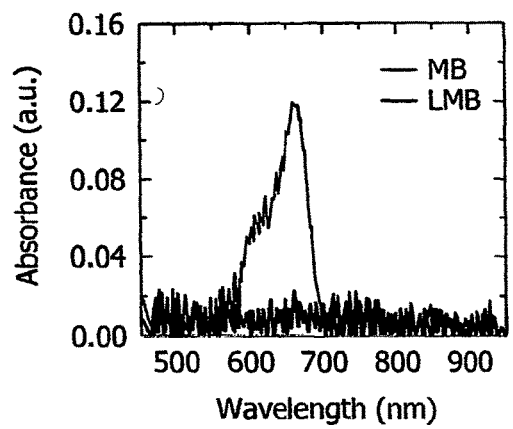

FIGS. 3A and 3B further show electrochemical reduction of Methylene Blue (MB) to Leucomethylene Blue (LMB). Note that FIG. 3B indicates a change absorbance between Leucomethylene Blue (LMB) and Methylene Blue (MB).

Figure 4A:
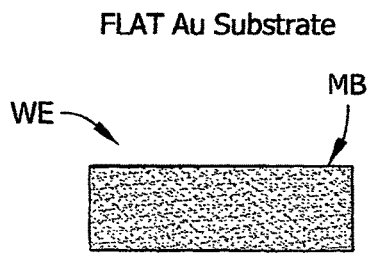
FIGS. 4A and 4B show a Methylene Blue layer created onto a flat surface area, and onto a surface comprising a multiplicity of regularly ordered nanostructures.
Figure 4B:
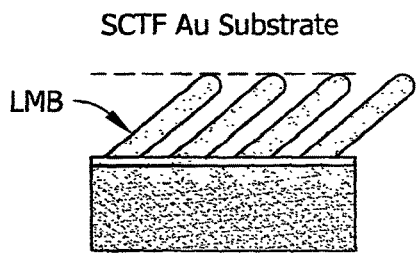

FIG. 4A shows a Methylene Blue (MB) layer created on a flat surface area of a Working Electrode (WE), which is transformed into FIG. 4B Leucomethylene Blue (LMB), (ie. a multiplicity of regularly ordered nanostructures projecting at an angle to the plane of the Working Electrode surface). Said transformation is brought about by application of a voltage between the Working Electrode (WE) and the Counter Electrode (CE) in such as a FIG. 1F system.

Figure 5:
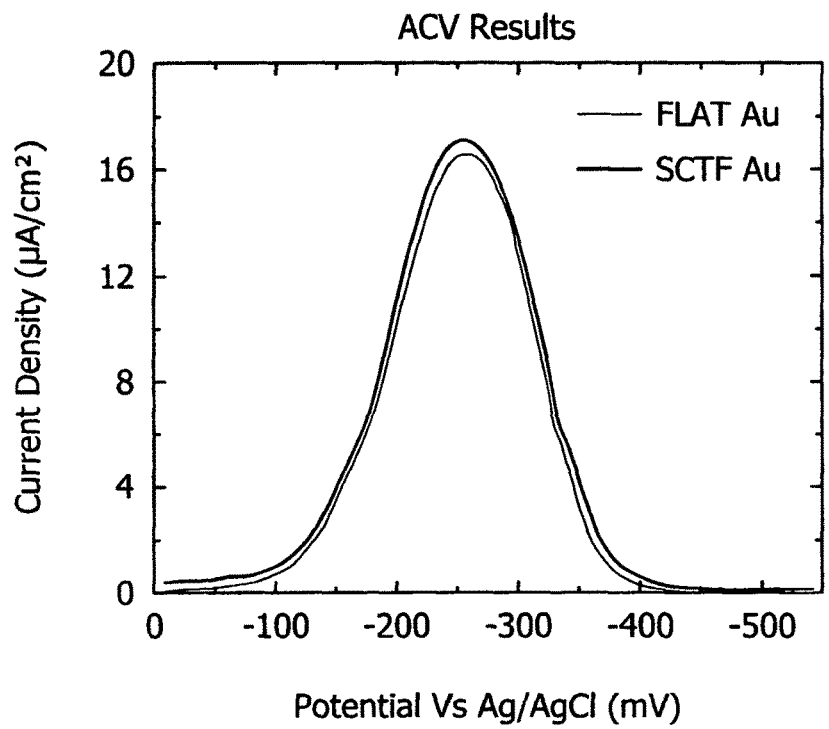
FIG. 5 shows an example of a current density electrical signal obtained during linear variation of the potential between a working electrode and a counter electrode.

FIG. 5 shows an example of a current density electrical signal obtained during linear variation of the potential between a working electrode and a counter electrode (Ag/AgCl) superimposed with a small 1 mv AC potential. The signals are collected on a Methylene Blue (MB) layer created on a flat Working Electrode (WE) which consists of gold (Au). The collected peak signal corresponds to the potential at which the Methylene Blue (MB) is reduced to Leucomethylene Blue (LMB), and is shown to be at about −270 mv.

Figure 6:
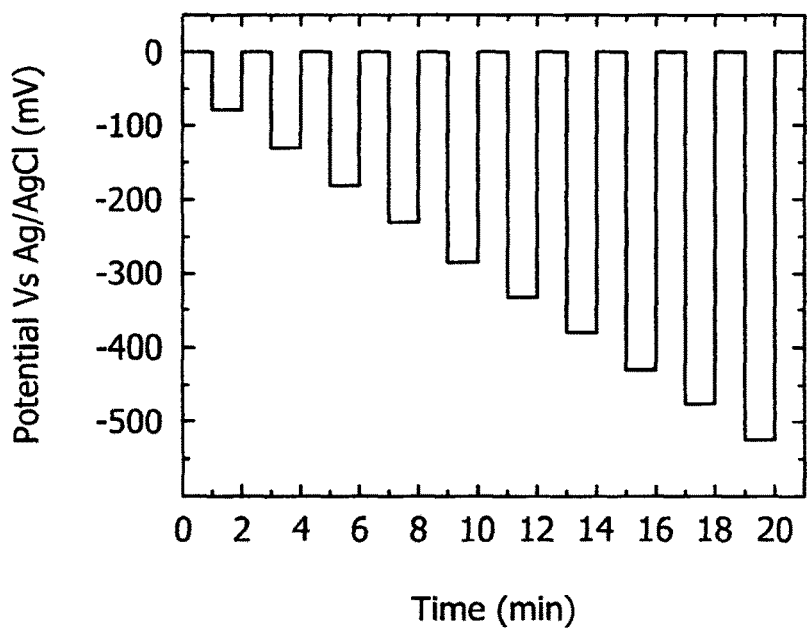
FIG. 6 shows an example of a time variation of the potential between working electrode and a counter electrode referenced to an Ag/AgCl reference electrode.

FIG. 6 shows an example of a time variation of the potential between working electrode and a counter electrode referenced to an Ag/AgCl reference electrode as shown in FIGS. 1e and 1f.

Figure 7A:
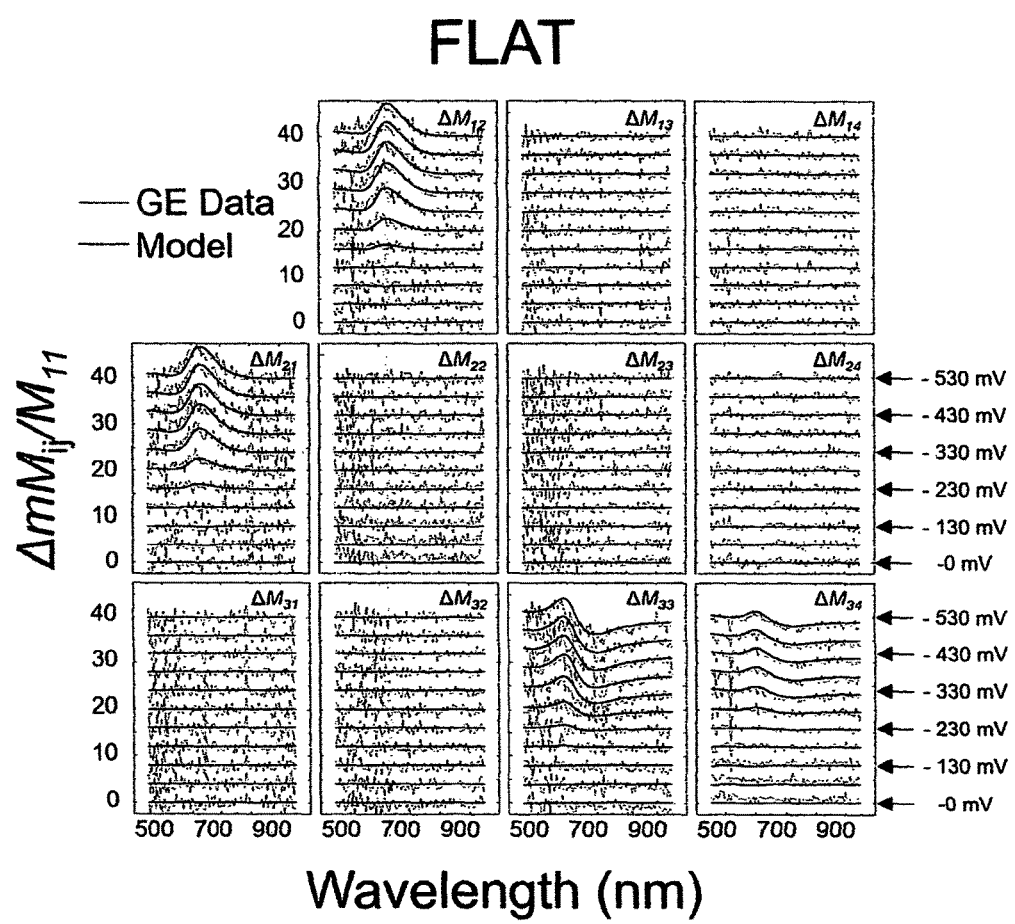
FIGS. 7A and 7B show examples of Mueller Matrix Ellipsometry data for a flat surface and for a surface comprising a multiplicity of regularly ordered nanostructures.
Figure 7B:
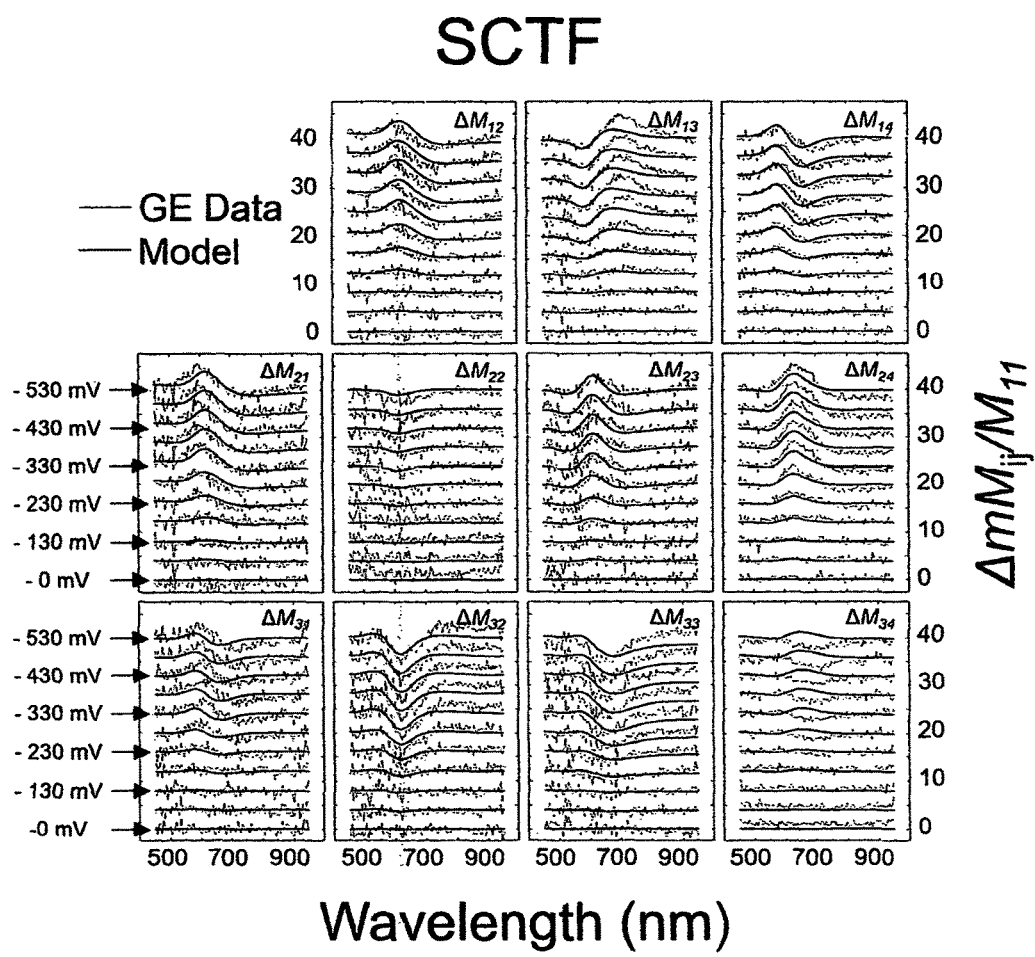

FIGS. 7A and 7B show examples of Mueller Matrix Ellipsometry data for a flat surface and for a surface comprising a multiplicity of regularly ordered nanostructures.

Figure 8A:
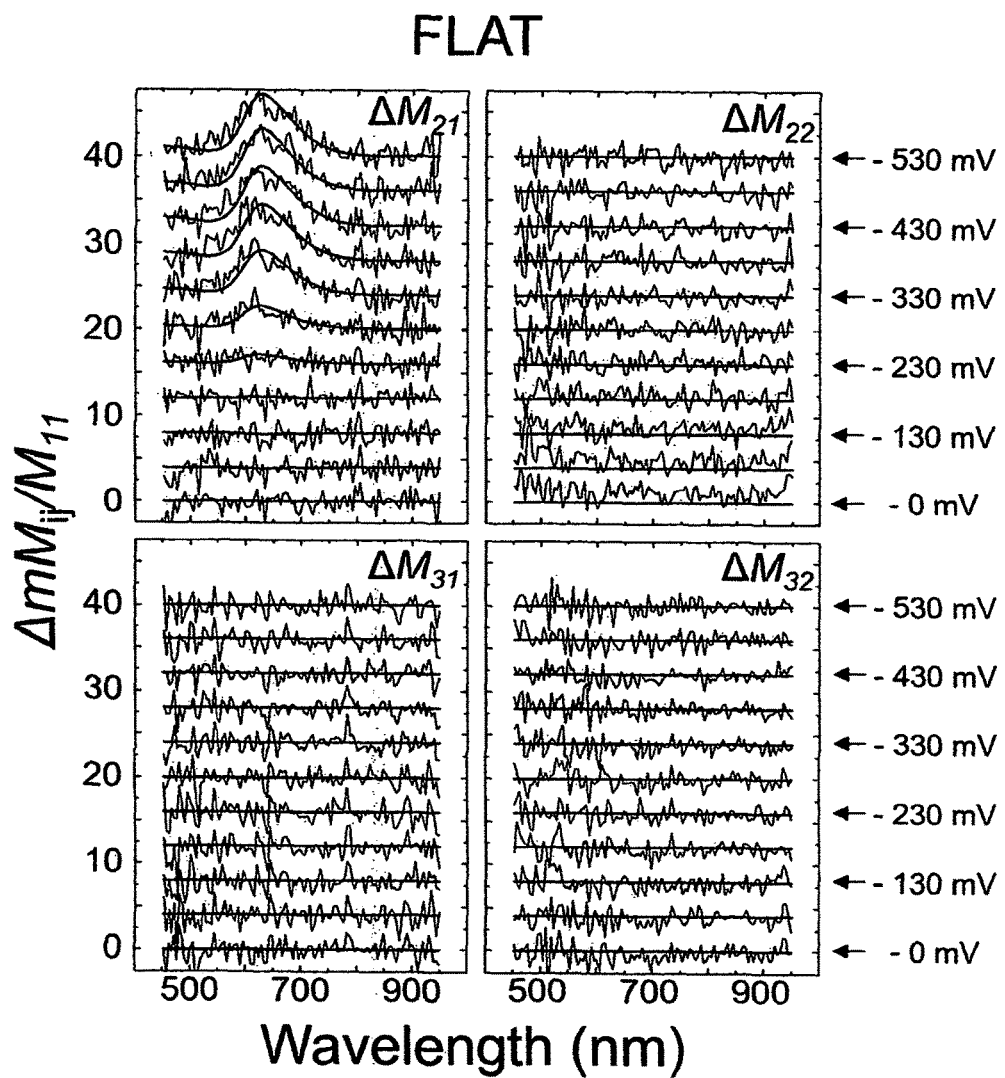
FIGS. 8A and 8B show examples for lower right 2×2 sub-blocks of the Mueller Matrix in FIGS. 7A and 7B with more clarity.
Figure 8B:
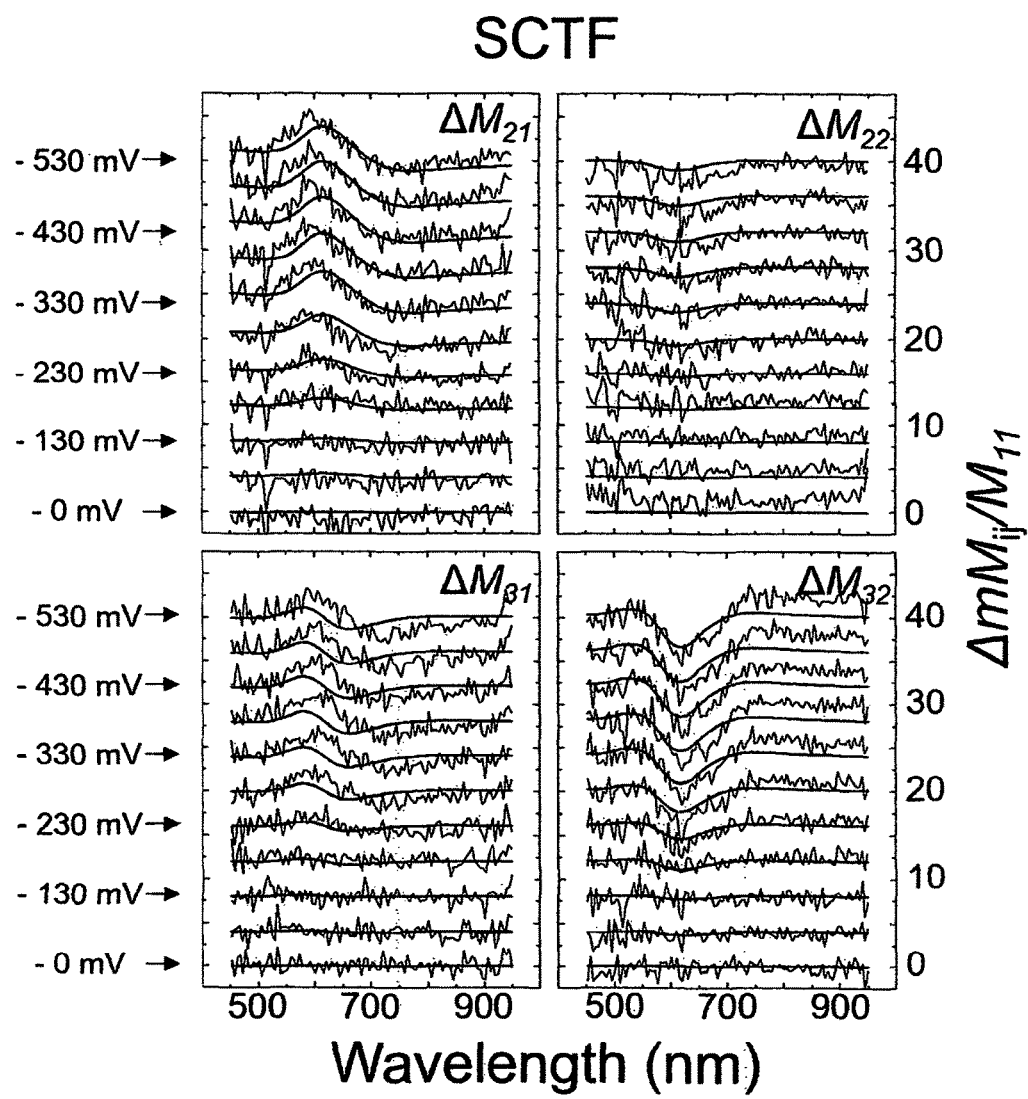

FIGS. 8A and 8B show examples for lower right 2×2 sub-blocks of the Mueller Matrix in FIGS. 7a and 7b for more clarity.

Figure 9:
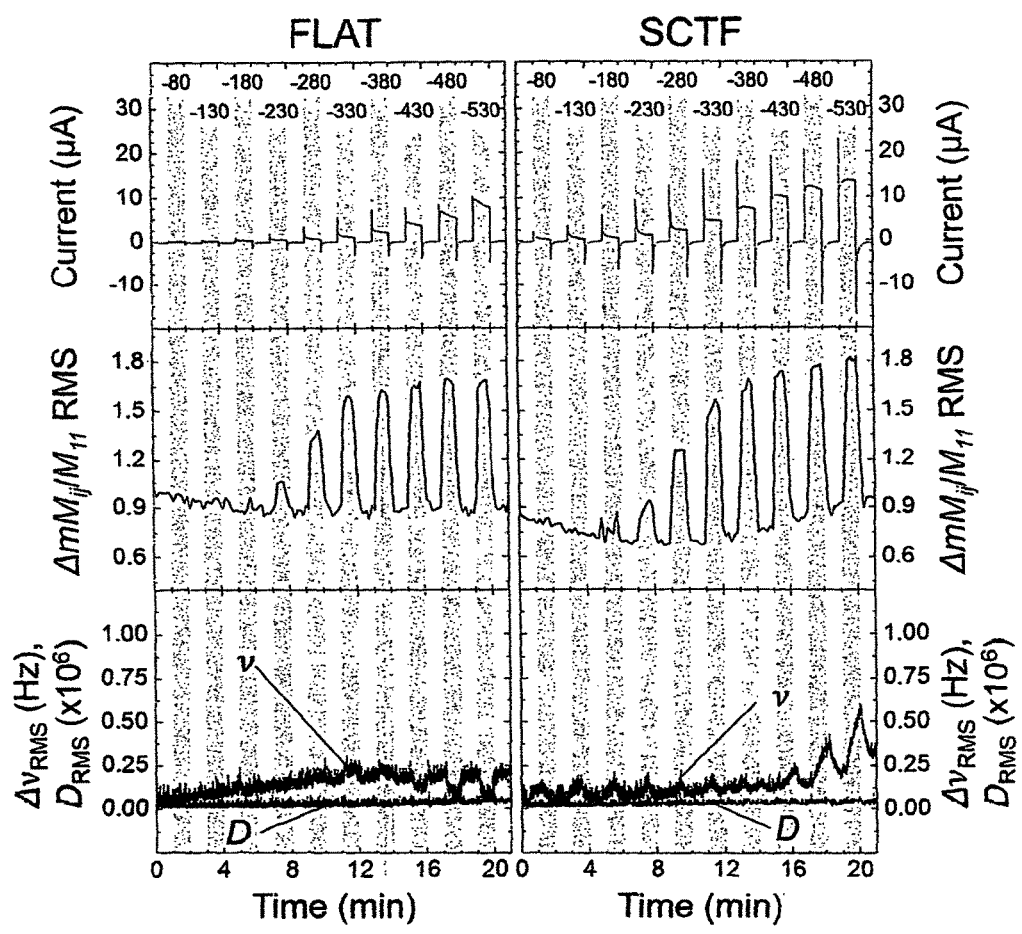
FIG. 9 shows an example of raw Mueller Matrix data signals collected while ramping the potential as indicated in FIG. 6.

FIG. 9 shows an example of raw data signals collected while ramping the potential as indicated in FIG. 6. The top row shows exemplary chronoampermetry data collected while ramping the potential shown in FIG. 6. The middle row shows raw ellipsometric data, and the third row shows piezoelectric crystal microbalance (piezoelectric micro balance) data obtained collected during the same potential ramping.

Figure 10:
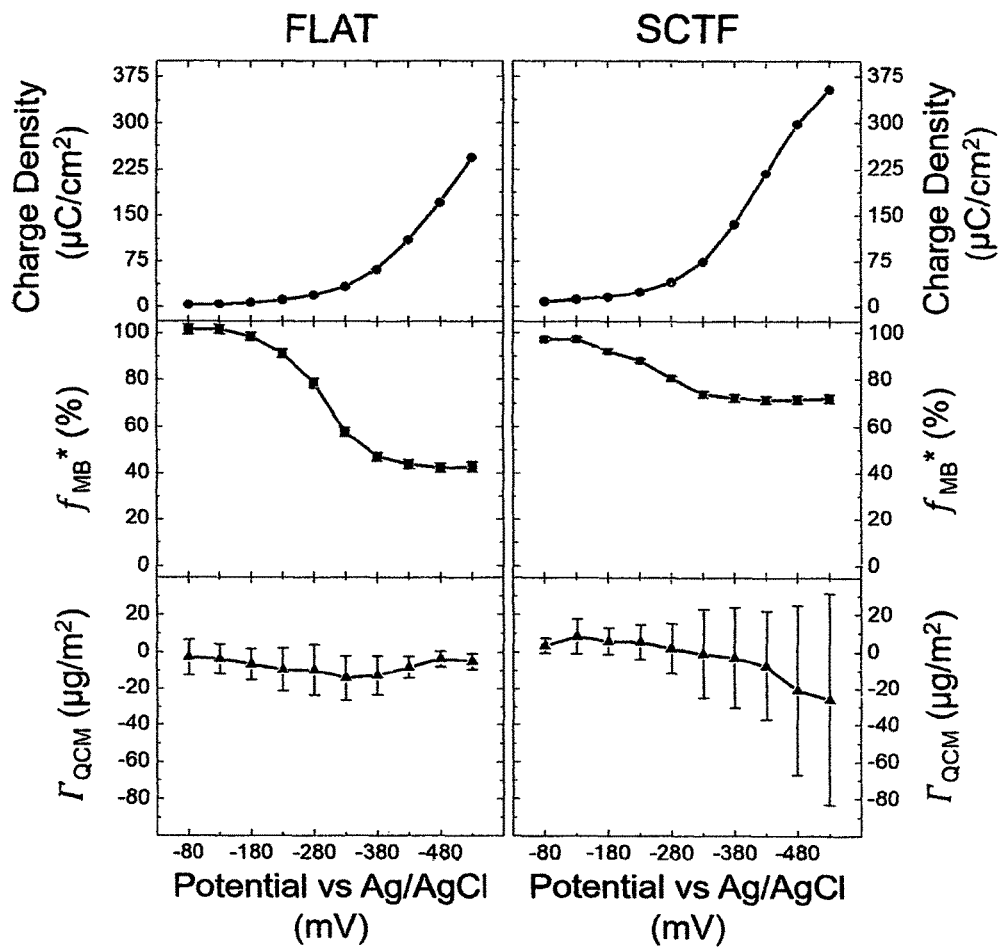
FIG. 10 shows model parameters obtained from raw signals as shown in FIG. 9 for the MB to LMB reduction.

FIG. 10 shows model parameters obtained from raw signals as shown in FIG. 9 for the MB to LMB reduction. The top row shows integrated electric charge collected by the working electrode. The middle row shows the fraction change of MB to LMB and the bottom row shows the change in mass attached to the working electrode.

While FIGS. 2A-10 are disclosing of a very interesting specific application of the present invention system, it is to be understood that the invention system primarily, though not exclusively, is found in the combination of an electrochemical cell that comprises a Piezoelectric Balance and capability of applying a Spectroscopic Ellipsometer to simultaneously investigate dynamic chemical processes that are catalyzed by application of an electrical potential between said Working Electrode (WE) and a Counter Electrode (CE), especially when the Working Electrode (WE) comprises fibers that project non-normal to the surface thereof, exemplified in FIGS. 2B and 4B. The method of the present invention enables simultaneously determining uncorrelated effective thickness and Optical Constants of a material electrochemically deposited onto said Working Electrode (WE), including investigation of anisotropic properties thereof from analysis of Ellipsometric data, in the form of off-axis elements of Jones and/or Mueller Matricies, derived therefrom.

Finally, it is noted that the terminology "piezoelectric balance" is used in this disclosure. Typically the preferred piezoelectric material is quartz.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for dynamically determining uncorrelated effective thickness and optical constants for a mass on a surface of a working electrode in a piezoelectric balance, and which enables simultaneous investigation of electrochemical driven reactions as a function of applied electrical energy, said piezoelectric balance comprising said working electrode that responds by vibrating when a potential is applied thereto, the frequency of vibration of the piezoelectric balance working electrode being dependent on the mass thereof; said working electrode being a component of an electrochemical cell, said electrochemical cell comprising an entry port for entering an electrolyte thereinto and a counter electrode, such that in use an electrolyte is entered into said entry port and contacts said working electrode, such that when electrical energy is applied between said working electrode and said counter electrode an electrochemical reaction occurs at the working electrode thereby causing a change in the vibrational frequency of said piezoelectric balance which is representative of a change in mass of, and thereby the effective thickness thereof, as a result of electrochemical reaction;

said system further comprising a source of electromagnetic radiation which is oriented to simultaneously direct a beam of electromagnetic radiation therefrom at the surface of said working electrode, interact therewith and enter a detector of electromagnetic radiation that produces data which, knowing the effective thickness of the mass at said working electrode, enables determining associated, uncorrelated optical constants for the effective thickness of the mass of the working electrode.

2. A system as in claim 1, which further comprises an exit port for flowing electrolyte out of said electrochemical cell.

3. A system as in claim 1, in which the working electrode comprises a multiplicity of nanostructures projecting from said working electrode surface normal, or non-normal thereto.

4. A system as in claim 1, in which the source of electromagnetic radiation and detector thereof are elements of an ellipsometer system that comprise polarization state generating and polarization state analyzing elements ahead of and after said working electrode, respectively.

5. A system as in claim 1, which further comprises on the surface of said working electrode, a multiplicity of nanostructures projecting non-normally therefrom.

6. A system as in claim 5, in which the source of electromagnetic radiation and detector thereof are elements of an ellipsometer system that comprise polarization state generating and polarization state analyzing elements ahead of and after said working electrode, respectively.

7. A system as in claim 1, in which the piezoelectric material comprising the working electrode is quartz.

8. A system as in claim 1, wherein the effective thickness of said mass of said working electrode is changed as a result of deposition of an analyte from said fluid thereonto from said fluid.

9. A system as in claim 1, wherein the effective thickness of said mass of said working electrode is changed as the result of etching material therefrom as a result of interaction with said fluid.

10. A system as in claim 1, which further comprises a reference electrode which is applied to establish a reference potential from which the potential applied between the working and counter electrodes can be calibrated.

11. A method of dynamically determining uncorrelated effective thickness and optical constants for a mass on a surface of a working electrode in a piezoelectric balance, and enables simultaneous investigation of electrochemical driven reactions as a function of applied electrical energy, comprising:

a) providing a system for dynamically determining uncorrelated effective thickness and optical constants for a mass on a surface of a working electrode in a piezoelectric balance, and which enables simultaneous investigation of electrochemical driven reactions as a function of applied electrical energy, said piezoelectric balance comprising said working electrode that responds by vibrating when a potential is applied thereto, the frequency of vibration of the piezoelectric balance working electrode being dependent on the mass thereof; said working electrode being a component of an electrochemical cell, said electrochemical cell comprising an entry port for entering an electrolyte thereinto and a counter electrode, such that in use an electrolyte is entered into said entry port and contacts said working electrode, such that when electrical energy is applied between said working electrode and said counter electrode an electrochemical reaction occurs at the working electrode thereby causing a change in the vibrational frequency of said piezoelectric balance which is representative of a change in mass of, and thereby the effective thickness thereof, as a result of electrochemical reaction;

said system further comprising a source of electromagnetic radiation which is oriented to simultaneously direct a beam of electromagnetic radiation therefrom at the surface of said working electrode, interact therewith and enter a detector of electromagnetic radiation that produces data which, knowing the effective thickness of the mass at said working electrode, enables determining associated, uncorrelated optical constants for the effective thickness of the mass of the working electrode;

b) causing electrolyte to flow into said entry port of said electrochemical cell and interact with said surface of said working electrode, while applying energy between said working and counter electrodes; and while applying vibration effecting potential to the working electrode of said piezoelectric balance;

c) simultaneously with step a) causing said source of electromagnetic radiation to direct a beam of electromagnetic radiation so that it interacts with said surface of said working electrode and enter said detector of electromagnetic radiation;

d) gleaning effective thickness of said mass of said working electrode and with that known, determining optical constants of said mass of said surface of working electrode.

12. A method as in claim 11, in which the step of providing a system further involves providing a working electrode that comprises a multiplicity of nanostructures projecting normally or non-normally from said surface of said working electrode.

13. A method as in claim 11, in which the step of providing a system further involves providing an exit port for flowing electrolyte out of said electrochemical cell.

14. A method as in claim 11, wherein the effective thickness of said mass of said working electrode is changed as a result of deposition of an analyte from said electrolyte thereonto from said fluid.

15. A method as in claim 11, wherein the effective thickness of said mass of said working electrode is changed as the result of said etching material therefrom as a result of interaction with said electrolyte.

16. A method as in claim 11, in which the step of providing a system further involves providing a reference electrode which is applied to establish a reference potential from which the potential applied between the working and counter electrodes can be calibrated.

17. A method of dynamically determining uncorrelated effective thickness and optical constants for a mass on a surface of a working electrode in a piezoelectric balance, comprising:

a) providing a system for dynamically determining uncorrelated effective thickness and optical constants for a mass on a surface of a working electrode in a piezoelectric balance, and which enables simultaneous investigation of electrochemical driven reactions as a function of applied electrical energy, said piezoelectric balance comprising said working electrode that responds by vibrating when a potential is applied thereto, the frequency of vibration of the piezoelectric balance working electrode being dependent on the mass thereof; said working electrode being a component of an electrochemical cell, said electrochemical cell comprising an entry port for entering an electrolyte thereinto and a counter electrode, such that in use an electrolyte is entered into said entry port and contacts said working electrode, such that when electrical energy is applied between said working electrode and said counter electrode an electrochemical reaction occurs at the working electrode thereby causing a change in the vibrational frequency of said piezoelectric balance which is representative of a change in mass of, and thereby the effective thickness thereof, as a result of electrochemical reaction;

said system further comprising a source of electromagnetic radiation which is oriented to simultaneously direct a beam of electromagnetic radiation therefrom at the surface of said working electrode, interact therewith and enter a detector of electromagnetic radiation that produces data which, knowing the effective thickness of the mass at said working electrode, enables determining associated, uncorrelated optical constants for the effective thickness of the mass of the working electrode;

said system being distinguished in that the surface of said working electrode comprises a multiplicity of nanostructures projecting non-normally therefrom;

b) entering a fluid into said entry port of said cell and interact with said surface of said working electrode while applying vibration effecting potential to the working electrode of said piezoelectric balance;

c) simultaneously with step a) causing said source of electromagnetic radiation to direct a beam of electromagnetic radiation so that it interacts with said surface of said working electrode and enter said detector of electromagnetic radiation;

d) gleaning effective thickness of said mass of said working electrode and with that known, determining optical constants of said mass of said surface of working electrode.

18. A method as in claim 17, in which the step of providing a system further involves providing an exit port for flowing electrolyte out of said electrochemical cell.

19. A method as in claim 17, wherein the effective thickness of said mass of said working electrode is changed as a result of deposition of an analyte from said electrolyte thereonto from said fluid.

20. A method as in claim 17, wherein the effective thickness of said mass of said working electrode is changed as the result of said etching material therefrom as a result of interaction with said electrolyte.

21. A method as in claim 17, in which the step of providing a system further involves providing a reference electrode which is applied to establish a reference potential from which the potential applied between the working and counter electrodes can be calibrated.

22. A method as in claim 17 which comprises determining at least partial Jones or Mueller Matricies from data provided by the detector of electromagnetic radiation in the process of determining optical constants.

23. A method as in claim 22 in which at least one off-diagonal Jones or Mueller matrix element is determined.

24. A method as in claim 17 which further comprises varying the voltage applied between the working electrode and counter electrode, while also simultaneously obtaining data regarding the frequency of vibration of said working electrode and ellipsometric data vs. said applied voltage between said working electrode and said counter electrode so that an electrochemical reaction occurs at the working electrode, thereby enabling simultaneous determination of uncorrelated sample optical constants and sample thickness, as well as sample changes as a function of applied voltage between said working electrode and said counter electrode.

\* \* \* \* \*